United States Patent
Kim et al.

(10) Patent No.: US 12,202,876 B2
(45) Date of Patent: Jan. 21, 2025

(54) TRANSMEMBRANE DOMAIN DERIVED FROM HUMAN LRRC24 PROTEIN

(71) Applicant: KOREA RESEARCH INSTITUTE OF CHEMICAL TECHNOLOGY, Daejeon (KR)

(72) Inventors: Seong Jun Kim, Daejeon (KR); Kyun Do Kim, Daejeon (KR); In Su Hwang, Daejeon (KR); Keunbon Ku, Daejeon (KR); Chonsaeng Kim, Daejeon (KR); Bum Tae Kim, Daejeon (KR); Dae Gyun Ahn, Daejeon (KR); Hae Soo Kim, Daejeon (KR); Young Chan Kwon, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 730 days.

(21) Appl. No.: 17/296,622

(22) PCT Filed: Dec. 16, 2019

(86) PCT No.: PCT/KR2019/017829
§ 371 (c)(1),
(2) Date: May 25, 2021

(87) PCT Pub. No.: WO2020/130547
PCT Pub. Date: Jun. 25, 2020

(65) Prior Publication Data
US 2022/0306718 A1    Sep. 29, 2022

(30) Foreign Application Priority Data

Dec. 19, 2018 (KR) .................. 10-2018-0165438
Nov. 13, 2019 (KR) .................. 10-2019-0144779

(51) Int. Cl.
*C07K 14/705* (2006.01)
*A61K 47/64* (2017.01)

(52) U.S. Cl.
CPC .......... *C07K 14/705* (2013.01); *A61K 47/645* (2017.08); *C07K 2319/03* (2013.01); *C07K 2319/60* (2013.01)

(58) Field of Classification Search
CPC ............ C07K 14/705; C07K 2319/03; C07K 2319/60; C07K 19/00; A61K 47/645; A61K 38/00; A61K 38/385; A61K 38/08; A61K 39/12; A61K 2039/6031; A61P 31/12
See application file for complete search history.

(56) References Cited

FOREIGN PATENT DOCUMENTS

| KR | 10-1799904 | 11/2017 | |
| KR | 20170128516 | 11/2017 | |
| KR | 10-1848147 | 4/2018 | |
| WO | WO-2004020595 A2 * | 3/2004 | ............ C07K 14/47 |
| WO | 2010-129033 | 11/2010 | |
| WO | 2013129698 | 9/2013 | |
| WO | 2014086835 | 6/2014 | |
| WO | 2016-161516 | 10/2016 | |
| WO | 2018109771 | 6/2018 | |

OTHER PUBLICATIONS

Wang et al (2014, Journal of Controlled Release, doi.org/10.1016/j.jconrel.2013.11.020, {herein Wang}. (Year: 2014).*
GenBank: BAD97811.1 (2005, https://www.ncbi.nlm.nih.gov/protein/BAD97811.1) {herein GenBank: BAD97811.1}. (Year: 2005).*
K Singh, Raushan, et al. "Protein engineering approaches in the post-genomic era." Current Protein and Peptide Science 19.1 (2018): 5-15. (Year: 2018).*
Zhang, Meiling, David A. Case, and Jeffrey W. Peng. "Propagated perturbations from a peripheral mutation show interactions supporting WW domain thermostability." Structure 26.11 (2018): 1474-1485. (Year: 2018).*
Database GenBank [online], Accession No. AB178281, May 3, 2015 uploaded, [retrieved on May 10, 2022], Definition: *Homo sapiens* mRNA for LRRC24 protein, complete cds, novel gene containing Leucine rich repeat.

(Continued)

*Primary Examiner* — Paul J Holland
*Assistant Examiner* — Erica Nicole Jones-Foster
(74) *Attorney, Agent, or Firm* — LEX IP MEISTER, PLLC

(57) ABSTRACT

The present invention relates to a transmembrane domain derived from human LRRC24 protein. More specifically, the present invention relates to a transmembrane domain derived from the human LRRC24 protein (LRRC24P transmembrane domain) or a cell-penetrating peptide, and an intracellular delivery system comprising same. The transmembrane domain derived from the human LRRC24 protein of the present invention can be used to deliver cargo materials such as compounds, biomolecules, and various polymer materials into cells. Since the LRRC24P transmembrane domain of the present invention exhibits higher cell penetration efficiency compared to conventional cell-penetrating peptides and is derived from human proteins, thus avoiding side effects and immune responses caused by peptides derived from foreign proteins, it can be usefully used as an effective intracellular delivery method for compounds, biomolecules, and various polymer materials applied to the human body.

10 Claims, 8 Drawing Sheets

Specification includes a Sequence Listing.

(56) References Cited

OTHER PUBLICATIONS

Strausberg et al., "*Homo sapiens* leucine rich repeat containing 24, mRNA (cDNA clone MGC:111484 Image:5767723), complete cds.", NCBI GenBank BC111067.1, https://www.ncbi.nlm.nih.gov/nuccore/BC111067.1, Jul. 21, 2006 (Jul. 21, 2006).
CIPO, Office Action of CA 3,122,428 dated Jun. 7, 2022.
Manoj Lakshmanan et al., "Rapid and Efficient Gene Delivery into Plant Cells Using Designed Peptide Carriers", Biomacromolecules 2013, 14, 1, 10-16, Dec. 6, 2012.
Sara R. Barkow et al. "Polypeptide Translocation by the AAA+ ClpXP Protease Machine", Chemistry & Biology, Current Biology, London, GB, vol. 16, No. 6, Jun. 26, 2009 (Jun. 26, 2009), pp. 605-612, XP026211465, ISSN: 1074-5521, DOI: 10.1016/J.CHEMBIOL.2009.05.007.
EPO, Search Report of EP 19898351.2 dated Aug. 3, 2022.
NCBI, Genbank Accession No. AAI11068.1 (Jul. 21, 2006).
KIPO, Office Action of KR 10-2019-0144779 dated Apr. 7, 2021.
M. C. Morris et al., "A new peptide vector for efficient delivery of oligonucleotides into mammalian cells", Nucleic Acids Research, 1997, vol. 25, No. 14, 2730-2736.
Sangho Lim et al., "dNP2 is a blood-brain barrier-permeable peptide enabling ctCTLA-4 protein delivery to ameliorate experimental autoimmune encephalomyelitis", Nature Communications vol. 6, Article No. 8244 , Sep. 15, 2015.
Je-Min Choi et al., "Intranasal delivery of the cytoplasmic domain of CTLA-4 using a novel protein transduction domain prevents allergic inflammation", Nat Med. May 2006;12(5):574-9. doi: 10.1038/nm1385. Epub Apr. 9, 2006.
Jinseu Park et al., "Mutational analysis of a human immunodeficiency virus type 1 Tat protein transduction domain which is required for delivery of an exogenous protein into mammalian cells", Journal of General Virology (2002), 83, 1173-1181.
Mazin Magzoub et al., "N-terminal peptides from unprocessed prion proteins enter cells by macropinocytosis", Biochemical and Biophysical Research Communications 348 (2006) 379-385, Jul. 24, 2006.
Daniele Derossi et al., "The third helix of the Antennapedia homeodomain translocates through biological membranes", J Biol Chem. Apr. 8, 1994;269(14):10444-50.

\* cited by examiner

TRANSMEMBRANE DOMAIN DERIVED FROM HUMAN LRRC24 PROTEIN

FIELD OF THE INVENTION

The present invention relates to a transmembrane domain derived from human LRRC24 protein and an intracellular delivery system comprising the same.

BACKGROUND OF THE INVENTION

Medicines used to treat diseases or alleviate symptoms are largely divided into low molecular weight compound pharmaceuticals and macromolecule biopharmaceuticals, and biomedicines include therapeutic proteins, antibodies, vaccines for prophylaxis or treatment, gene therapy, and cell therapy. In particular, recombinant protein pharmaceuticals are mass-produced using gene recombination technology for therapeutic proteins that are difficult to produce in vivo. In the early 1980s, after Recombinant human insulin for diabetes treatment was first approved by the US FDA, various recombinant protein drugs such as growth hormone, erythropoietin, interferon, colony stimulating factor (CSF), and blood factors have been released. However, compared to low molecular compound drugs that pass through the cell membrane and enter the cell to show their activity relatively easily, most of the macromolecule substances, including recombinant proteins and nucleic acids, are very difficult to deliver into cells, making it difficult to show efficacy as drugs. Therefore, methods using electroporation, microinjection, cationic lipid vesicle, viral vector, virus-like-particles, etc., have been used or studied for intracellular delivery of macromolecule substances. However, the above methods are difficult to use directly into the human body, or are difficult to inject again into the human body after delivery to cells isolated from the human body, and accordingly, there is a difficulty in increasing time and cost. Also, it may cause side effects that induce apoptosis or an immune response in vivo, which has a great limitation in its application.

Researches for the development of new drug delivery systems and macromolecule biopharmaceuticals that can overcome the above problems are actively being conducted, and a representative method among them is a carrier known as Protein Transduction Domain (PTD) or Cell Penetrating Peptides, (CPP). Cell-penetrating Peptides were first discovered to have the property of passing through the cell membrane of the TAT protein of the HIV virus and the polypeptides (GRKKRRQRRRPPG (SEQ ID NO: 27), RKKRRQRRR (SEQ ID NO: 28), YGRKKRRQRRR (SEQ ID NO: 29)) present in the TAT protein, after that new cell penetrating peptides such as Penetratin derived from *Drosophila* (RQIKIWFQNRRMKWKK (SEQ ID NO: 30)), MPG derived from HIV glycoprotein 41 (GALFLGFL-GAAGSTMGAWSQPKKKRKV (SEQ ID NO: 31)), BPrPr derived from bovine prion protein (MVKSKIGSWIL-VLFVAGPSDVGLCKKRP (SEQ ID NO: 32)), Hph-1 derived from human Hph-1 protein (YARVRRRGPRR (SEQ ID NO: 33)) and NP2 derived from human NLBP protein (KIKKVKKKGRK (SEQ ID NO: 34)) have been developed. Since then, studies using the above cell-penetrating peptides have been actively conducted, and it has been found that cargo substances such as DNA, siRNA, PNA (Peptide nucleic acid), proteins, and liposome nanoparticles can be effectively delivered into cells.

Previous studies have shown that cell-penetrating peptides are energy-independent through direct penetration and can deliver macromolecule substances into cells even at low temperatures, and it has been found that permeation through endocytosis is also possible.

Currently, cell-penetrating peptides are being developed for Cerebral ischemia and Alzheimer's disease treatment using TAT-JBD20, development of amyotrophic lateral sclerosis treatment using TAT-BH4, and preclinical experiments such as cancer treatment using MPG-8/siRNA and TAT-DRBD/siRNA are in progress. Also, the development of a treatment for myocardial infarction using TAT-6 PKC inhibitor, a treatment for hearing loss and inflammation using TAT-JBD20, and a treatment for brain tumor using p28 are in clinical trials.

As described above, research on cell-penetrating peptides and the development of various candidate drugs using the same are actively progressing, but there are problems to be overcome, and for this purpose, it is necessary to develop a new cell-penetrating peptide that can improve cell penetration efficiency and minimize side effects and unintended immune responses in vivo caused by the cell-penetrating peptide and the cargo material associated therewith.

Therefore, in order to overcome the disadvantages that the existing cell-penetrating peptides were mainly invented from proteins derived from non-humans such as viruses and *drosophila*, or have low penetration efficiency, among the human-derived peptides, a cell-penetrating peptide with high penetration efficiency, a cell-penetrating peptide derived from human LRRC24 (Leucine rich repeat containing 24) protein, was invented, and peptides present in human-derived proteins were identified for similarity with existing cell-penetrating peptides, and the present invention was completed through this.

As prior documents, the following non-patent documents were referenced.

1. Mutational analysis of a human immunodeficiency virus type 1 Tat protein transduction domain which is required for delivery of an exogenous protein into mammalian cells. J. Gen. Virol., 83 (2002), pp. 1173-1181
2. The third helix of the Antennapedia homeodomain translocates through biological membranes. J. Biol. Chem., 269 (1994), pp. 10444-10450
3. A new peptide vector for efficient delivery of oligonucleotides into mammalian cells. Nucleic Acids Res. 14 (1997) pp. 2730-2736.
4. N-terminal peptides from unprocessed prion proteins enter cells by macropinocytosis. Biochem. Biophys. Res. Commun., 348 (2006), pp. 379-385
5. Intranasal delivery of the cytoplasmic domain of CTLA-4 using a novel protein transduction domain prevents allergic inflammation. Nat Med, 12 (2006), pp. 574-579
6. dNP2 is a blood-brain barrier-permeable peptide enabling ctCTLA-4 protein delivery to ameliorate experimental autoimmune encephalomyelitis. Nat Commun. 8244 (2015), pp. 1-13

DETAILED DESCRIPTION OF THE INVENTION

Summary

An object of the present invention is to provide a novel transmembrane domain capable of minimizing side effects and exhibiting high cell penetration efficiency.

Another object of the present invention is to provide an intracellular delivery system comprising a transmembrane domain to which a cargo of an intracellular transport object is bound to the terminal of a peptide.

Another object of the present invention is to provide a method of transporting a cargo into a cell comprising the step of contacting a transmembrane domain in which a cargo of an intracellular transport object is bound to the terminal of a peptide.

Technical Solution

In order to achieve the above object, the present invention is to provide a transmembrane domain comprising a polypeptide of any one of SEQ ID NOs: 1 to 22 derived from human LRRC24 (Leucine rich repeat containing 24) protein.

In the present invention, the term "cell penetrating peptide (CPP)" refers to a peptide having the ability to transport the cargo of the object to be transported into cells in vitro and/or in vivo, and is used interchangeably with "transmembrane domain".

Also, in the present invention, the term 'peptide' refers to a macromolecule in the form of a chain formed by bonding of 4 to 1000 amino acid residues to each other by a peptide bond, and is used interchangeably with 'polypeptide'.

In the present invention, unlike cell penetrating peptides derived from existing viruses or other species, in order to minimize side effects that occur when cargo material is delivered through cell penetrating peptides into the human body, since it is a peptide present in human-derived proteins, compared to existing cell penetrating peptides, it provides a new human-derived transmembrane domain or cell penetrating peptide that has a very high delivery efficiency into cells and can minimize side effects when treated to the human body.

The present invention provides a recombinant cargo having improved cell membrane permeability including a cargo fused to the N-terminus or C-terminus of the transmembrane domain and the transmembrane domain.

The cargo may be a protein, nucleic acid, lipid, or a recombinant cargo that is a compound. Also, the cargo may be an adjuvant or an antigen.

According to one embodiment, the cargo may be a recombinant cargo selected from the group of hormones, immunoglobulins, antibodies, structural proteins, signaling peptides, storage peptides, membrane peptides, transmembrane peptides, internal peptides, external peptides, secretory peptides, viral peptides, native peptides, glycosylated proteins, fragmented protein, disulfide peptides, recombinant proteins, chemically modified proteins, and prions.

Also, the term 'recombinant cargo' in the present invention refers to a complex formed by recombination of a transmembrane domain and one or more cargos by genetic fusion or chemical bonding.

Also, the term 'contact' in the present invention means that the cargo is in contact with a eukaryotic or prokaryotic cell, and by such contact, the cargo is transferred into the eukaryotic or prokaryotic cell.

Also, in the present invention, the introduction of proteins, peptides, etc. into cells is interchangeably used with expressions of transport, penetration, transport, delivery or passage.

Also, according to one embodiment, the cargo may be a recombinant cargo selected from the group consisting of nucleic acids, coding nucleic acid sequences, mRNA, antisense RNA molecules, carbohydrates, lipids, and glycolipids.

Also, according to one embodiment, the cargo may be a contrast material, a drug or a recombinant cargo that is a chemical substance.

In the present invention, the term 'contrast material' means all materials used for the contrast of a living body structure or fluid in medical imaging. The contrast material may include a radiopaque contrast material, a paramagnetic contrast material, a superparamagnetic contrast material, a CT contrast material, or other contrast material, but is not limited thereto.

Examples may include radiopaque metals and salts thereof (e.g. silver, gold platinum, etc.) and other radiopaque chemicals (e.g., calcium salts, barium salts such as barium sulfate, tantalum and tantalum oxide). Paramagnetic contrast material (for MR imaging) may include gadolinium dientylene triaminepentaacetic acid and derivatives thereof and other gadolinium, manganese, iron, dysprosium, copper europium, erbium, chromium, nickel and cobalt complex hydroxybenzylethylene diamine diacetic acid (HBED). The superparamagnetic contrast material (for MR imaging) may include magnetite, superparamagnetic iron oxide, superfine iron oxide, superparamagnetic iron oxide, and monocrystalline iron oxide. Other suitable contrast material may include iodination and non iodination, ionic and nonionic CR compositions, and contrast material such as spin-labels, or other diagnostic actives. When expressed in cells, it may contain a marker gene encoding an easily detectable protein. Various labels such as radionuclides, fluorescent substances, enzyme cofactors, enzyme inhibitors, etc. may be used.

As an example, when the cargo according to the present invention is a protein or a peptide, by binding the DNA expressing the transfer peptide to the DNA expressing the transfer target and then expressing it, the transfer peptide and the transfer target can be combined in the form of a fusion protein of the transfer target and the peptide. Specific examples of binding by fusion proteins are as follows: When making a primer to produce a fusion protein, after attaching the nucleotide encoding the transport peptide in front of the nucleotide expressing the transfer object, the obtained nucleotide is inserted into a vector (eg. PET vector) with a restriction enzyme, and BL-21 (DE3) is transformed into cells for expression. At this time, when an expression inducer such as IPTG (Isopropylβ-D-1-thiogalactopyranosid) is treated to purify the fusion protein and then PBS is treated, the transport peptide may be combined with a dyeing substance or a fluorescent substance, specifically fluorescein isothiocyanate (FITC), luciferase (Luciferase, Luc), Green fluorescent protein, GFP, enhanced green fluorescent protein, EGFP, Tag GFP, Superfolder GFP, PA GFP, AcGFP, PS-GFP2, Yellow fluorescent protein, YFP, enhanced Yellow fluorescent protein, EYFP, SYFP, TagYFP, PhiYFP, Azurite, mKalamal, Cyan fluorescent protein, CFP, enhanced Cyan fluorescent protein, ECFP, TagCFP, PS-CFP2, Red fluorescent protein, RFP, Tag RFP, Tag RFP657, mRFP1, PaTagRFP, Turbo RFP, RFP693, tdRFP, Blue fluorescent protein, BFP, mTag BFP, Yellow-green fluorescent protein, mNeongreen, Bright monomeric fluorescent protein, Scarlet-i, mplum, monomeric cherry fluorescent protein, mcherry, PAmcherry, monomeric strawberry fluorescent proteins, mStrawberry, monomeric orange fluorescent protein, mOrange, PSmOrange, mRasberry, mKate, mKate2, monomeric teal fluorescent protein, mTFP, mNeptune, mRubby, mRubby2, mBanana, Discosoma sp, red fluorescent protein, DSRed, mCitrine, Emerald, T-Sapphire, mApple, mgrape, Venus, Topaz, J-Red, tdTomato, mTurquoise, mTurquosie2, mKO, mKO2, mUKG. IFP1.4, mEos2, mEos4, mHoneydew, Dronpa, katushka, Ypet, CyPet, Clover, kaede, KikGR, mTangerine, Zsgreen, ZsYellow, Cerulean, Beta-galactosidase, LacZ, β-lactamase, BLA, Beta-glucuronidase, GUS, Alkaline phosphatase, chloramphenicol acetyltransferase or peroxidase.

According to another aspect of the present invention, the present invention provides a gene construct comprising a polynucleotide encoding the transmembrane domain.

Also, the present invention provides an expression vector for expressing a recombinant cargo protein having improved cell penetration efficiency, including a gene construct.

The present invention also provides a method for preventing or treating diseases such as cervical cancer, prostate cancer, ovarian cancer, endometrial cancer, uterine cancer, bladder cancer, esophageal cancer, head and neck cancer, Wilms tumor, soft tissue sarcoma, stomach cancer, pancreatic cancer, breast cancer, bronchial cancer, etc., comprising the step of administering to an individual a pharmaceutical composition comprising a conjugate in which a physiologically active peptide is bound to the transmembrane domain and a pharmaceutically acceptable carrier.

The pharmaceutical compositions according to the present invention may be formulated in the form of oral dosage forms such as powders, granules, tablets, capsules, suspensions, emulsions, syrup, aerosols, etc., or external preparations, suppositories, and sterile injectable solutions according to a conventional method.

Carriers, excipients, and diluents that may be included in the composition include lactose, Textrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydride Oxybenzoate, propylhydroxybenzoate, talc, magnesium stearate, and mineral oil.

In the case of formulation, it is prepared using diluents or excipients such as fillers, extenders, binders, wetting agents, disintegrants, and surfactants that are usually used. Solid preparations for oral administration include tablets, pills, powders, granules, capsules, etc., and these solid preparations are prepared by mixing at least one excipient such as starch, calcium carbonate, sucrose or lactose, gelatin, and the like with the extract. In addition to simple excipients, lubricants such as magnesium stearate and talc are also used. Liquid preparations for oral use include suspensions, liquid solutions, emulsions, syrups, etc., and various excipients in addition to water and liquid paraffin, which are commonly used simple diluents, may include wetting agents, sweeteners, fragrances, and preservatives. Formulations for parenteral administration include sterilized aqueous solutions, non-aqueous solutions, suspensions, emulsions, lyophilized formulations, and suppositories.

As the non-aqueous solvent suspension, propylene glycol, polyethylene glycol, vegetable oil such as olive oil, and injectable ester such as ethyloleate may be used. As a base for suppositories, witepsol, macrogol, tween61, cacao butter, laurinji, glycerogelatin, and the like can be used.

The preferred dosage of the composition of the present invention varies depending on the condition and weight of the patient, the severity of the disease, the form of the drug, the route and duration of administration, but may be appropriately selected by those skilled in the art. However, for a desirable effect, the composition of the present invention is preferably administered at 0.0001 to 500 mg/kg per day, preferably 0.001 to 250 mg/kg. Administration may be administered once a day, or may be divided several times. The above dosage does not limit the scope of the present invention in any way.

According to another aspect of the present invention, the present invention provides a method of delivering a cargo into a cell comprising the steps of preparing a recombinant cargo in which cargo is fused to the N-terminus or C-terminus of the transmembrane domain; and contacting the prepared recombinant cargo with the isolated cells.

According to another aspect of the present invention, the present invention provides a method of delivering a cargo into an animal comprising the steps of preparing a recombinant cargo in which cargo is fused to the N-terminus or C-terminus of the transmembrane domain; and administering the prepared recombinant cargo to animals other than humans.

There are no conditions specifically required for contact between the transmembrane domain and the cell membrane, such as limited time, temperature, and concentration, and may be carried out under general conditions applied to cell penetration in the art.

Effects of the Invention

The cell-penetrating peptide of the present invention exhibits significantly improved cell penetration efficiency or cell permeability compared to the existing peptide, so that the transported cargo or biologically active molecule is introduced into the cell, effectively maintains its activity, and can greatly reduce the cost.

Also, it is possible to increase the effect of the cargo material delivered through the cell-penetrating peptide or the transmembrane domain.

Also, since it is a cell-penetrating peptide derived from a human protein, side effects caused by peptides derived from a non-human protein can be minimized.

However, the effects of the present invention are not limited to the above-mentioned effects, and other effects not mentioned will be clearly understood by those skilled in the art from the following description.

DETAILED DESCRIPTION

Figure 1:
FIG. 1 shows a schematic diagram of a gene synthesis for making a gene synthesis expressing the LRRC24P-EGFP recombinant fusion protein.

Unless otherwise defined herein, all technical and scientific terms used have the same meaning as commonly understood by one of ordinary skill in the art. A variety of scientific events including terms included herein are well known and available in the art.

The present invention provides a transmembrane domain or a cell-penetrating peptide comprising a polypeptide of any one of SEQ ID NOs: 1 to 22 derived from human LRRC24 (Leucine rich repeat containing 24) protein.

Conventional cell-penetrating peptides are mainly invented from proteins derived from non-humans such as viruses and *drosophila*, or have a disadvantage of low penetration efficiency. To overcome this, the present inventors discovered the LRRC24P peptide consisting of amino acid sequences 427 to 436 in human LRRC24 protein, which is expected to have cell permeability among human-derived peptides.

The cell-penetrating peptide represented by SEQ ID NO: 1 is a cell-penetrating peptide of LRRC24P consisting of amino acid sequences 427 to 436 in human LRRC24 protein, and the amino acid and nucleotide sequence information used for the invention is as follows.

```
1. LRRC24P peptide amino acid sequence
(SEQ ID NO: 1): RRRRRRKKAR

2. LRRC24P expression gene nucleic sequence
(SEQ ID NO: 23): cgccggcgccgcaggcgaaaaaaggcgcgg 3. LRRC24P gene synthesis nucleic sequence
(SEQ ID NO: 24): cgccgccgtagaagacgtaaaaaggcaaga
```

In the case of gene synthesis, for codon optimization, the conversion was used as described above. In order to verify cell permeability, the nucleic sequence information of the LRRC24P-EGFP fusion protein (253 amino acids) expressing the EGFP (Enhanced Green fluorescent protein) linked behind the nucleic sequence expressing the LRRC24P peptide (253 amino acids) is the same as the nucleic sequence 25, and the nucleic sequence of the linker portion between the LRRC24P cell-penetrating peptide or the transmembrane domain and the EGFP protein used in the Examples described in SEQ ID NO: 26 is ggaggtggggctcg. The LRRC24P cell-penetrating peptide has 10 amino acids, is hydrophilic and has a positive charge.

The cell-penetrating peptide or transmembrane domain represented by SEQ ID NOs: 2 to 22 of the present invention is a mutant cell-penetrating peptide of the LRRC24P cell-penetrating peptide, and is the LRRC24P mutant in which alanine, the 9th amino acid of LRRC24P is substituted with another amino acid, and the mutant transmembrane domain or cell-penetrating peptide of LRRC24P in which the N-terminal and C-terminal amino acids are deleted one by one respectively. The human LRRC24 protein-derived transmembrane domain or cell-penetrating peptide of the present invention is shown in Table 1 below.

TABLE 1

Human LRRC24 protein-derived transmembrane domain or cell-penetrating peptide

| Sequence number | Sequence name | Sequence) |
|---|---|---|
| Sequence number 1 | LRRC24P | RRRRRRKKAR |
| Sequence number 2 | LRRC24P-M1 | RRRRRRKKSR |
| Sequence number 3 | LRRC24P-M2 | RRRRRRKKVR |
| Sequence number 4 | LRRC24P-M3 | RRRRRRKKYR |
| Sequence number 5 | LRRC24P-M4 | RRRRRRKKER |
| Sequence number 6 | LRRC24P-M5 | RRRRRRKKQR |
| Sequence number 7 | LRRC24P-M6 | RRRRRRKKRR |
| Sequence number 8 | LRRC24P-MN | RRRRRRKKNR |
| Sequence number 9 | LRRC24P-MD | RRRRRRKKDR |
| Sequence number 10 | LRRC24P-MC | RRRRRRKKCR |
| Sequence number 11 | LRRC24P-MG | RRRRRRKKGR |
| Sequence number 12 | LRRC24P-MH | RRRRRRKKHR |
| Sequence number 13 | LRRC24P-MI | RRRRRRKKIR |
| Sequence number 14 | LRRC24P-ML | RRRRRRKKLR |
| Sequence number 15 | LRRC24P-MK | RRRRRRKKKR |
| Sequence number 16 | LRRC24P-MM | RRRRRRKKMR |
| Sequence number 17 | LRRC24P-MF | RRRRRRKKFR |
| Sequence number 18 | LRRC24P-MP | RRRRRRKKPR |
| Sequence number 19 | LRRC24P-MT | RRRRRRKKTR |
| Sequence number 20 | LRRC24P-MW | RRRRRRKKWR |
| Sequence number 21 | LRRC24P-M7 | RRRRRRKKAR |
| Sequence number 22 | LRRC24P-M8 | RRRRRRKKA |

Advantages and features of the present invention, and a method of achieving them will become apparent with reference to the embodiments described below in detail. Hereinafter, the present invention will be described in more detail by examples. However, the following examples are merely illustrative of the present invention and are not intended to limit the contents of the present invention to the following examples.

<Example 1> Construction of a Plasmid Vector Expressing a Protein Fused with a Human LRRC24 Protein-Derived Cell-Penetrating Peptide (LRRC24P) and an EGFP Fluorescent Protein In order to test the cell penetration efficiency of LRRC24, artificial gene synthesis was performed as follows. As shown in FIG. 1, 5'-NheI restriction enzyme recognition sequence-LRRC24P nucleic sequence-Linker nucleic sequence-EGFP protein nucleic sequence-termination codon-XhoI restriction enzyme recognition sequence-3' was synthesized.

Figure 2:
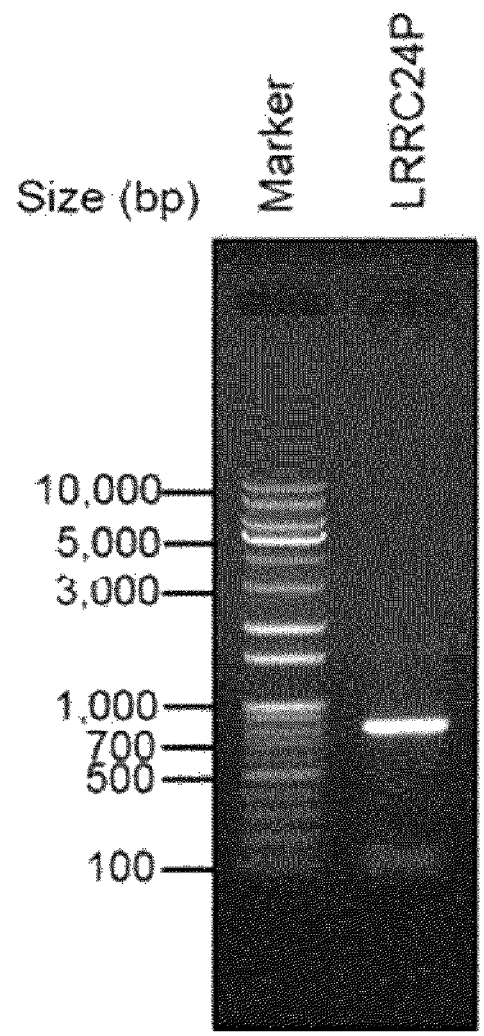
FIG. 2 shows the observation of a gene composition expressing a protein fused with a cell-penetrating peptide LRRC24P derived from a human LRRC24 protein and an Enhanced Green Fluorescent Protein (EGFP) fluorescent protein through agarose gel electrophoresis.
Figure 3:
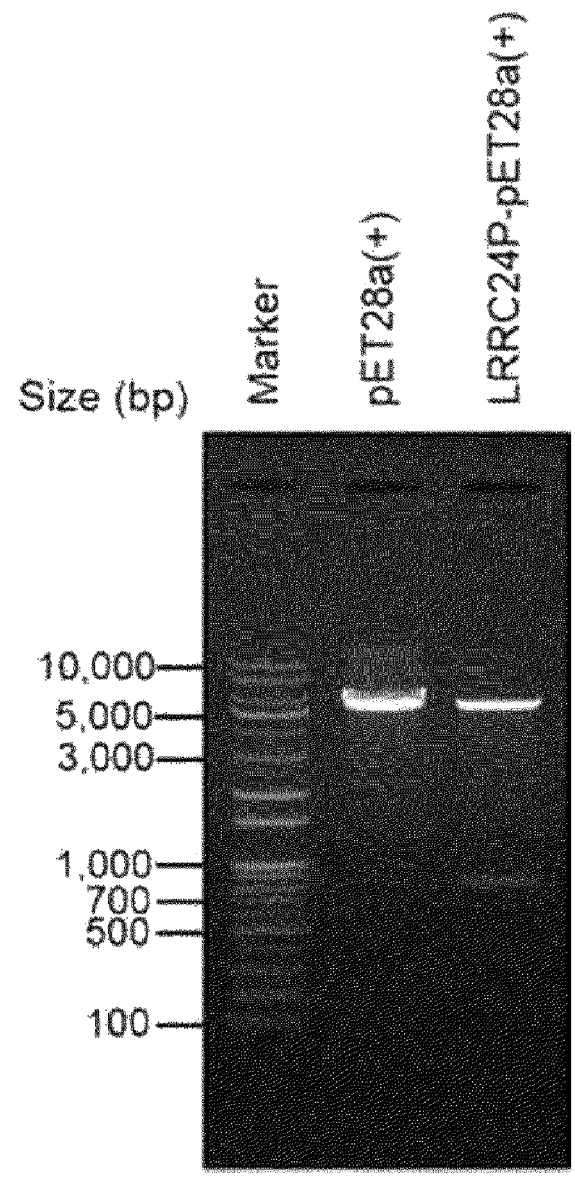
FIG. 3 shows that the LRRC24P-EGFP gene compound was inserted into the protein expression vector pET28a+, and the resultant was confirmed by treating the bound gene compound with a restriction enzyme.

In particular, the LRRC24P nucleic sequence was converted to a nucleic sequence expressing the same peptide through codon optimization when synthesizing an artificial gene, and to verify cell permeability, a gene expressing an EGFP fluorescent protein was attached to the nucleic sequence of the LRRC24P cell-penetrating peptide, followed by synthesis (FIG. 2). Also, a linker sequence was added between the cell-penetrating peptide and the EGFP protein to increase flexibility. After treatment of artificial synthetic gene with NheI restriction enzyme and XhoI restriction enzyme, similarly, it was introduced into pET28a+ plasmid vector treated with NheI restriction enzyme and XhoI restriction enzyme through T4 ligase. The pET-28a plasmid vector used here expresses 6 histidines (6×His) at the N-terminus in front of the LRRC24P-EGFP fusion protein, enabling protein purification through Ni-NTA Resin. The pET28a+ plasmid vector into which the LRRC24P-EGFP fusion protein artificial gene was introduced was transformed into Top 10 receptor cells, then cultured on an LB agar plate containing kanamycin, and the grown colonies were cultured in LB medium for about 16 hours. After that, a plasmid was obtained through a DNA extraction experiment, treated with NheI restriction enzyme and XhoI restriction enzyme, and then it was confirmed that the artificial gene of LRRC24P-EGFP fusion protein was successfully introduced into the pET-28a plasmid vector through agarose gel electrophoresis. (FIG. 3).

Figure 4:
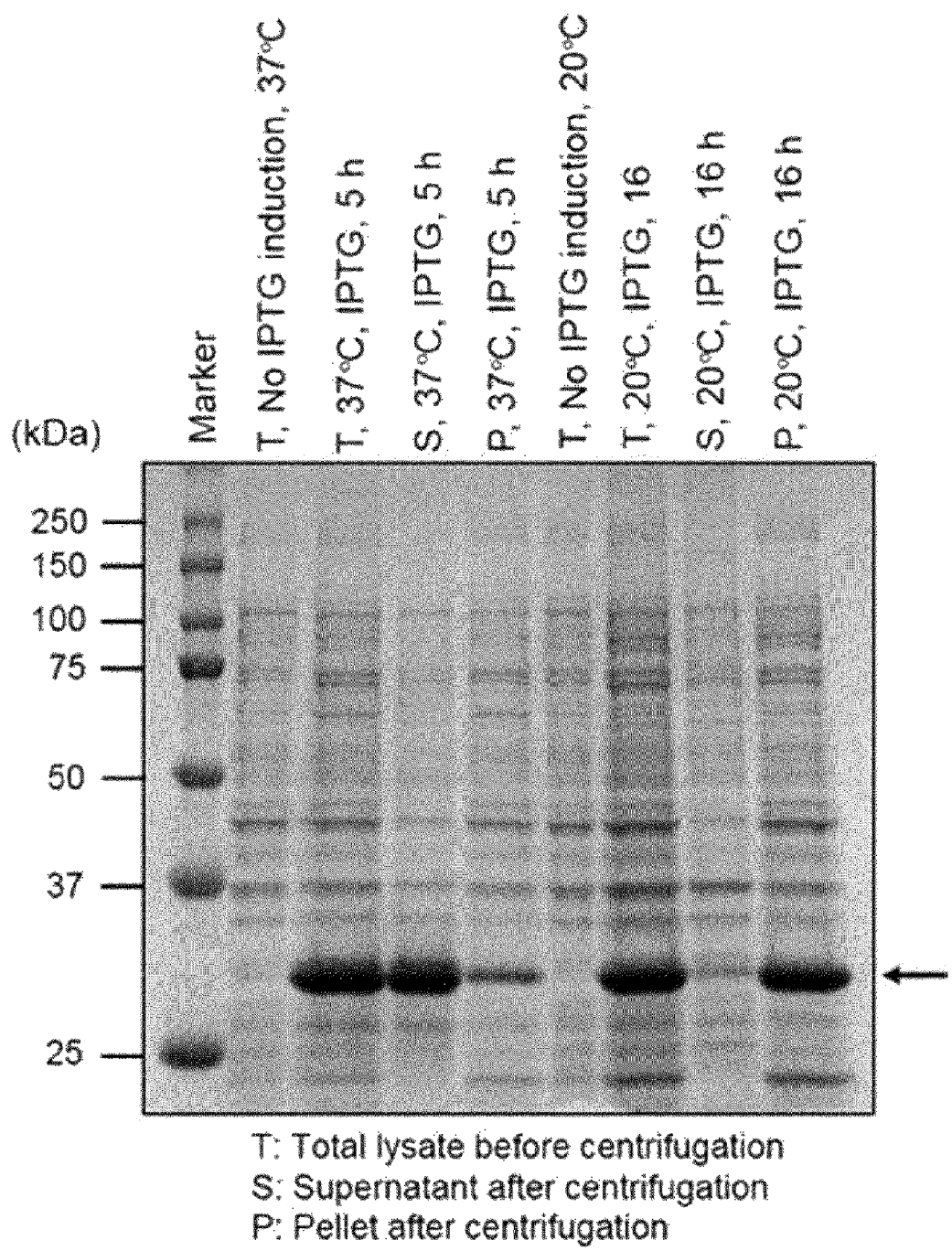
FIG. 4 shows that the LRRC24P-EGFP-pET28a+ vector was transformed into Rosetta (DE3) recipient cells, followed by induction of protein production and ultrasonic digestion, followed by polyacrylamide gel electrophoresis.

<Example 2> Establishment of Expression Conditions and High Purity Purification of a Protein in which a Human LRRC24 Protein-Derived Cell-Penetrating Peptide (LRRC24P) and EGFP Fluorescent Protein are Fused To establish the expression conditions of a protein fused with a cell-penetrating peptide (LRRC24P) derived from human LRRC24 protein and EGFP fluorescent protein, the plasmid vector prepared in Example 1 was transformed into Rosetta (DE3) recipient cells, and then incubated for about 16 hours in LB medium containing kanamycin. After adding 100 times of LB medium to this and incubate until the O.D value reaches 0.4-0.6, and add IPTG (Isopropyl β) to a final concentration of 1 mM, incubate at 37° C. for 5 hours or 20° C. for 16 hours. After that, the cells obtained by centrifugation were sonicated, and then separated into a supernatant and a cell pellet by centrifugation, and the expressed amount and water solubility of the protein were confirmed by polyacrylamide gel electrophoresis and Coomassie blue staining. (FIG. 4).

Through this, it was confirmed that the LRRC24P-EGFP fusion protein increased the water solubility and expression efficiency of the protein under the condition of incubating at 20° C. for 16 hours after the addition of IPTG. Therefore, in order to purify the high purity LRRC24P-EGFP fusion protein, the transformed Rosetta (DE3) recipient cells were cultured under the same conditions, and the culture medium was centrifuged to obtain a cell pellet, and suspended in lysis buffer (50 mM NaH2PO4, 300 mM NaCl, 10 mM Imidazole).

Figure 5:
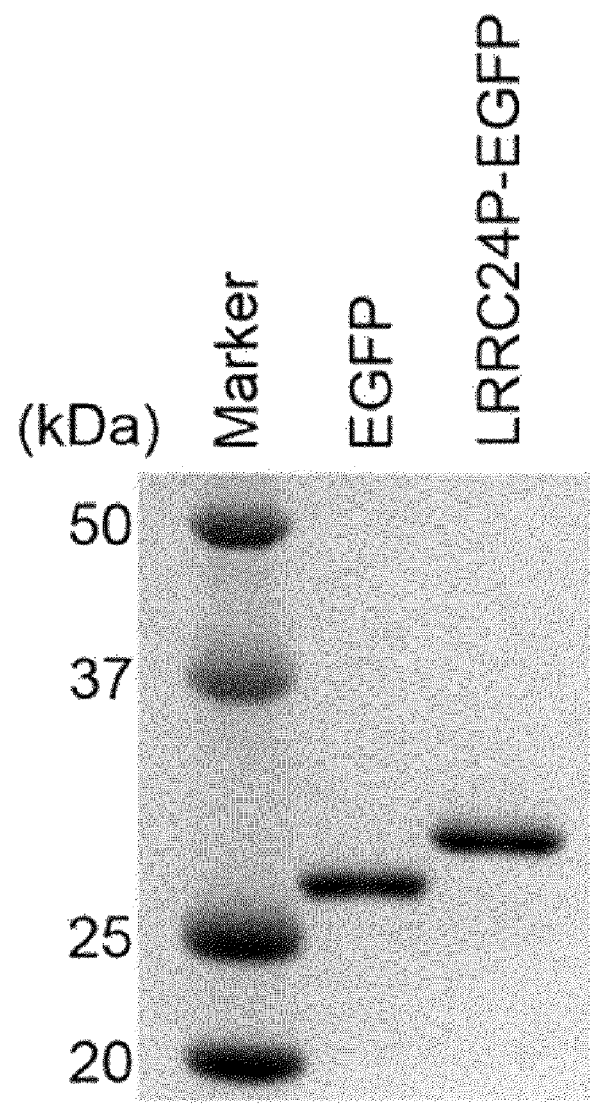
FIG. 5 shows that the LRRC24P-EGFP recombinant fusion protein produced using Rosetta (DE3) recipient cells was purified and observed through polyacrylamide gel electrophoresis.

The supernatant was collected by ultrasonic decomposition and centrifuged again, filtered through a 45 μm filter, and then passed through the supernatant through a Ni-NTA agarose column to bind the recombinant protein. To remove the protein non-specifically bound to the Ni-NTA agarose column, the Ni-NTA agarose column was washed with a washing buffer (50 mM NaH$_2$PO$_4$, 300 mM NaCl, 20 mM Imidazole), and then, to recover the recombinant protein bound to the Ni-NTA agarose column, the recombinant protein was eluted using an elution buffer (50 mM NaH$_2$PO$_4$, 300 mM NaCl, 500 mM Imidazole). After replacing the solution containing the LRRC24P-EGFP fusion protein with PBS using a PD-10 desalting column, it was confirmed through polyacrylamide gel electrophoresis and Coomassie blue staining (FIG. 5).

Figure 6:
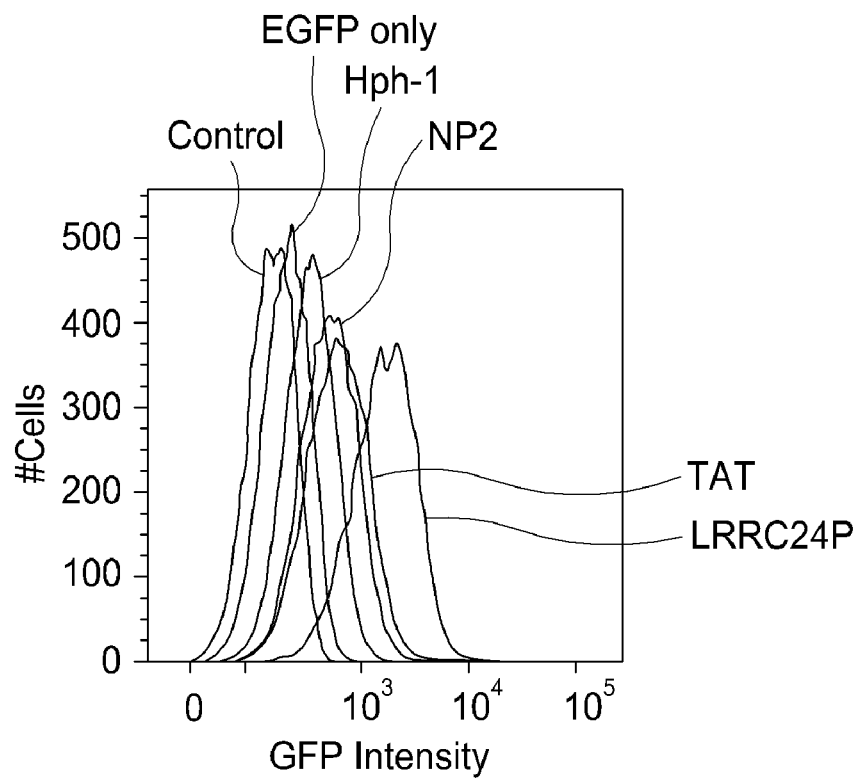
FIG. 6 shows a comparison of intracellular penetration efficiency by flow cytometry after treating a recombinant protein in which a conventional cell-penetrating peptide is fused with EGFP and the LRRC24P-EGFP recombinant protein in a human T immune cell line (Jurkat).
Figure 6:
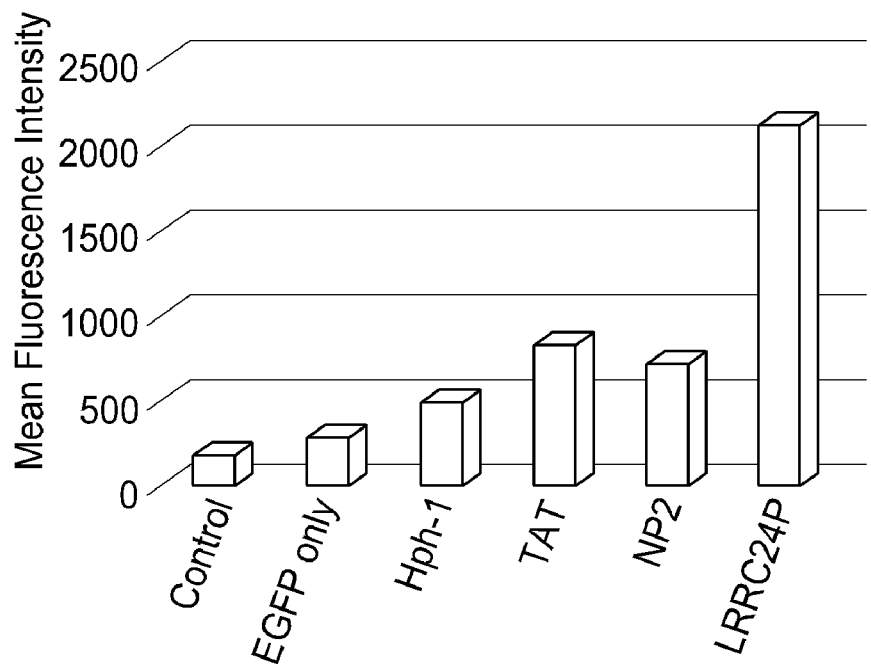

<Example 3> Confirmation of Intracellular Delivery Efficiency of LRRC24P-EGFP Fusion Protein In order to study the intracellular delivery efficiency of the LRRC24P-EGFP fusion protein, plasmid vectors expressing proteins in which EGFP fluorescent proteins are fused respectively were constructed in the same manner as plasmid vectors expressing LRRC24P-EGFP fusion proteins, to cell-penetrating peptides previously known Cell penetrating peptide (CPP), TAT (amino acid sequence: YGRKKRRQRRR (SEQ ID NO: 35), Diabetes 2001 August; 50 (8): 1706-1713, Proteins Linked to a Protein Transduction Domain Efficiently Transduce Pancreatic Islets), Hph-1 (amino acid sequence: YARVRRRGPRR (SEQ ID NO: 36), Nature Medicine 12 (5): 574-9, June 2006, Intranasal delivery of the cytoplasmic domain of CTLA-4 using a novel protein transduction domain prevents allergic inflammation) and NP2 (amino acid sequence: KIKKVKKKGRK (SEQ ID NO: 37), Nature Communications volume 6, Article number: 8244 (2015), dNP2 is a blood-brain barrier-permeable peptide enabling ctCTLA-4 protein delivery to ameliorate experimental autoimmune encephalomyelitis). Expression and purification of the existing CPP-EGFP fusion protein was also performed in the same manner as the LRRC24P-EGFP fusion protein. For cell experiments, after dispensing Jurkat cells 1.5×10$^6$/well into a 24 well plate, CPP-EGFP fusion protein was treated with a final concentration of 5 UM by floating in 2 ml of RPMI 1640 medium containing 10% Fetal Bovine Serum and 1% penicillin/streptomycin, and incubated for 2 hours in a 5% CO2 incubator maintained at 37° C. Thereafter, the medium containing the cells was transferred to a 5 ml tube, centrifuged to remove the supernatant, and washing with PBS solution was repeated three times. Thereafter, Jurkat cells were suspended in 650 μl of PBS, and the fluorescence of the CPP-EGFP fusion proteins introduced into the cells was measured through a flow cytometer to confirm the intracellular introduction efficiency (FIG. 6). Through this, it was confirmed that the LRRC24P cell-penetrating peptide exhibited about 3-5 times the efficiency compared to the existing cell-penetrating peptides (FIG. 6).

TABLE 2

Recombinant protein used in Example 3
Recombinant protein used in Example 3

| | |
|---|---|
| Negative control | Wild type EGFP |
| Experimental group | Fusion protein of recombinant LRRC24P purified in Example 2, LRRC24P-EGFP |
| Positive control | TAT-EGFP |
| | (Hph-1)-EGFP |
| | NP2 EGFP |

Figure 7:
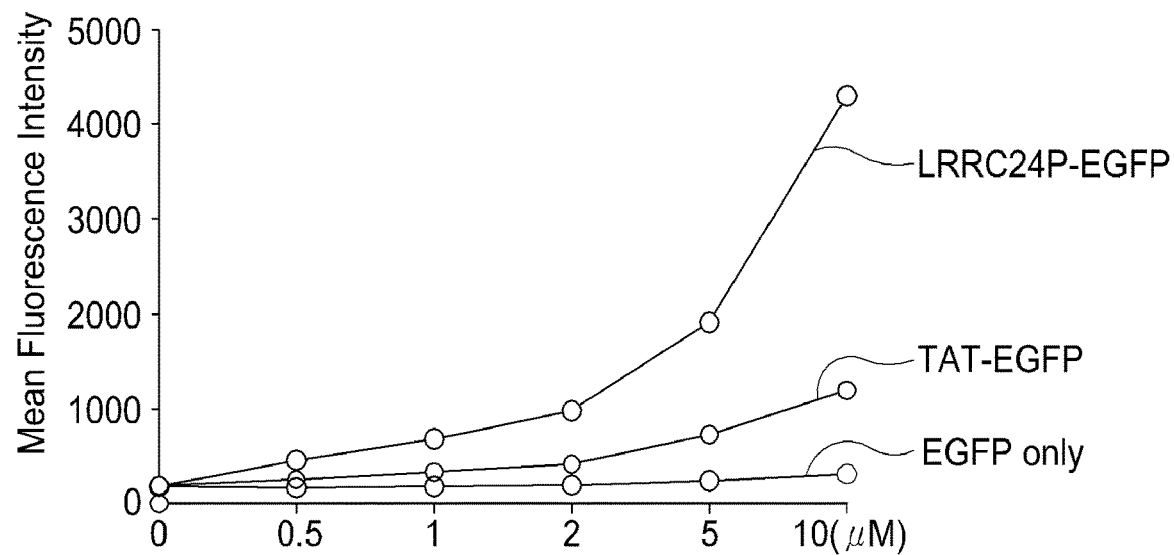
FIG. 7 shows the comparison of intracellular penetration efficiency by flow cytometry after processing the recombinant proteins fused with the cell-penetrating peptide by concentration.

In order to confirm the introduction efficiency of the LRRC24P-EGFP fusion protein by concentration, a comparative experiment was conducted using the EGFP protein and the fusion proteins of TAT and EGFP, which are currently the most widely used cell-penetrating peptides. EGFP, TAT-EGFP, and LRRC24P-EGFP fusion proteins were treated to Jurkat cells at final concentrations of 0.5, 1, 2, 5, and 10 μM, and the introduction efficiency was confirmed through the same process as the previous experiment. (FIG. 7). Through this, it was confirmed that the LRRC24P-EGFP fusion protein was introduced into the cells in a concentration-dependent manner, and compared with the TAT-EGFP fusion protein, it was confirmed that the delivery efficiency was significantly higher at all concentrations.

Figure 8:
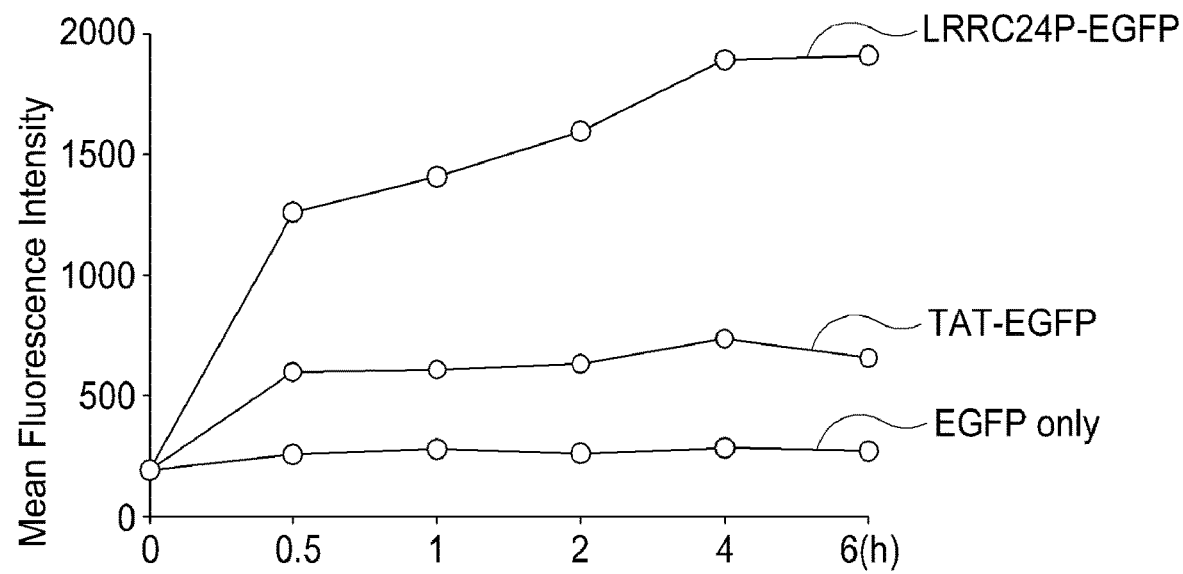
FIG. 8 shows the comparison of intracellular penetration efficiency by a flow cytometer after processing the recombinant proteins fused with the cell-penetrating peptide by time.

Next, in order to check the introduction efficiency of the LRRC24P-EGFP fusion protein over time, a comparative experiment was performed using EGFP and TAT-EGFP fusion proteins. EGFP, TAT-EGFP, and LRRC24P-EGFP fusion proteins were treated on Jurkat cells at a final concentration of 5 μM, respectively, and cultured for 0.5, 1, 2, 4, and 6 hours, respectively, and the introduction efficiency was confirmed through the same procedure as the previous experiment (FIG. 8). Through this, it was confirmed that the LRRC24P-EGFP fusion protein was introduced into the cell in a time-dependent manner, and compared with the TAT-EGFP fusion protein, it was confirmed that the delivery efficiency was significantly higher at all times.

Figure 9:
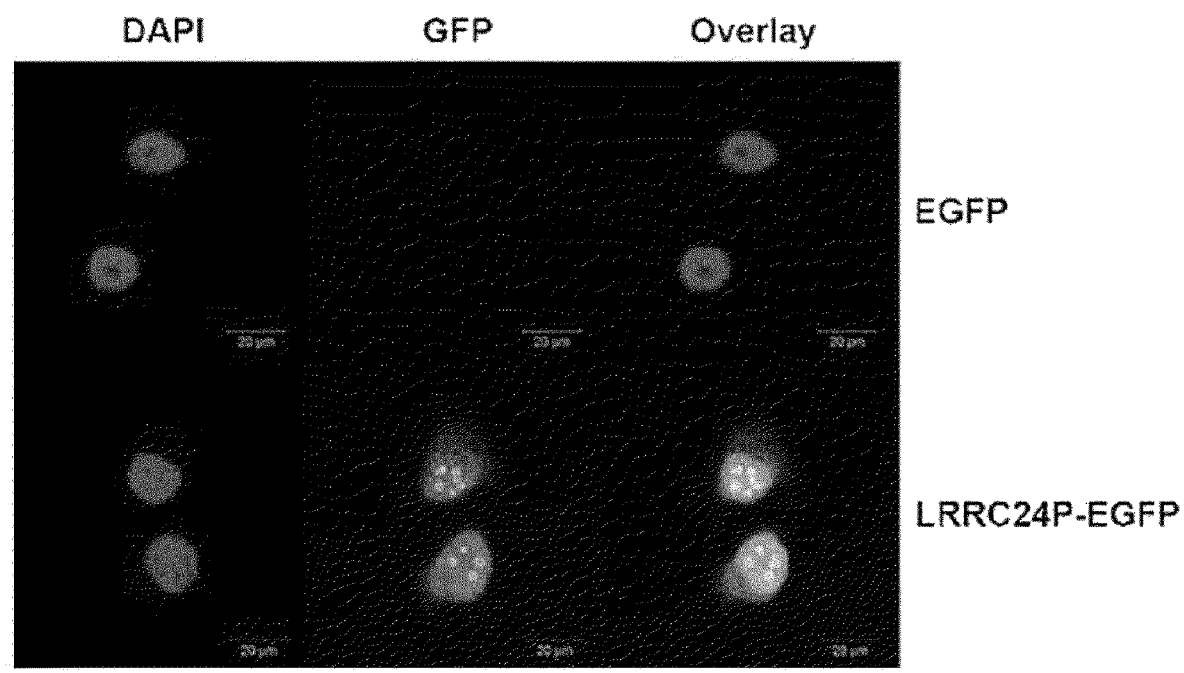
FIG. 9 shows the distribution pattern of the LRRC24P-EGFP recombinant protein permeated into the cell using a confocal microscope after treatment with the LRRC24P-EGFP recombinant protein in a cervical cancer cell line (HeLa).

<Example 4> Confirmation of Intracellular Delivery of LRRC24P-EGFP Fusion Protein To confirm the LRRC24P-EGFP fusion protein introduced into the cell with a confocal microscope, first, dispensing HeLa cells into a 24 well cell culture slide at $2\times10^4$/well, and then suspending them in 500 μl of DMEM medium containing 10% Fetal Bovine Serum and 1% penicillin/streptomycin, and incubated for 18 hours in a 5% $CO_2$ incubator maintained at 37° C. Thereafter, the cells were treated with EGFP and LRRC24P-EGFP fusion proteins at a final concentration of 1 μM, respectively, and cultured for 1 hour. Thereafter, the culture solution was removed, washed 3 times with a PBS solution, and then treated with a 4% PFA solution at room temperature for 30 minutes to fix. After removing the PFA solution, it was washed again with PBS solution 3 times, treated with the mounting medium, covered the cover slide, and observed with a confocal microscope. (FIG. 9) Through this, it was confirmed that the LRRC24P-EGFP fusion protein was effectively introduced into HeLa cells.

Figure 10:
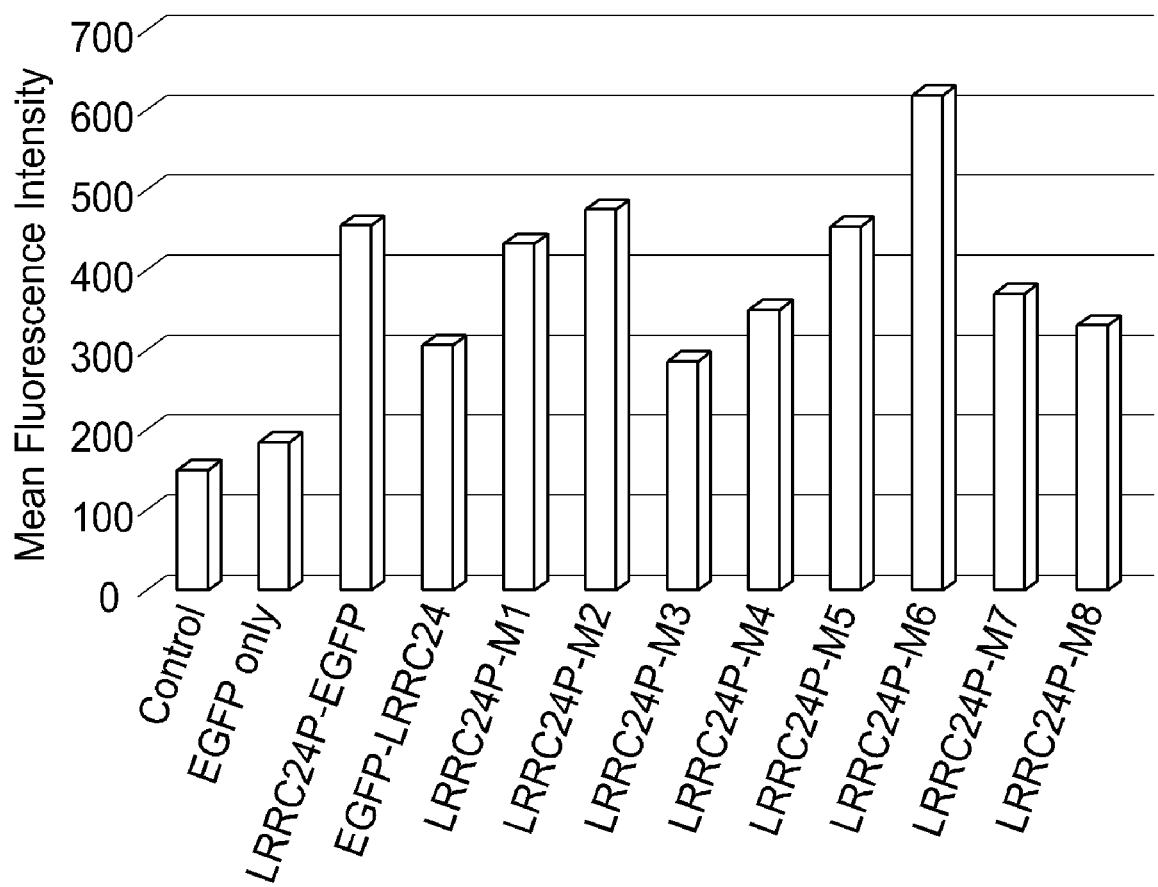
FIG. 10 shows the results of confirming the intracellular transduction efficiency of the LRRC24P mutant-EGFP fusion protein of the present invention after treatment with a human T immune cell line (Jurkat) and then using a flow cytometer (FACS).

<Example 5> Confirmation of Intracellular Delivery Efficiency of LRRC24P Mutant-EGFP Fusion Protein To confirm the intracellular delivery efficiency of the LRRC24P cell penetrating peptide mutant, after designing the LRRC24P mutant (mutation) in which alanine, the 9th amino acid of LRRC24P is substituted with another amino acid, and the LRRC24P mutant in which the amino acids at the N-terminal and C-terminals are deleted one by one, a plasmid vector expressing the LRRC24 mutant-EGFP fusion protein was constructed, and then the protein was expressed and purified. Among the LRRC24P cell penetrating peptide mutations of the present invention, cell experiments were conducted with the sequence name LRRC24P M1 to M8 (SEQ ID NOs: 2 to 7, or SEQ ID NOs: 21 and 28) peptides. For the cell experiment, Jurkat cells were dispensed into a 24 well plate at $1.5\times10^6$/well, and suspended in 2 ml of RPMI 1640 medium containing 10% Fetal Bovine Serum and 1% penicillin/streptomycin and treated with LRRC24P-EGFP and LRRC24P mutant-EGFP fusion proteins at a final concentration of 5 μM, and then incubated for 2 hours in a 5% $CO_2$ incubator maintained at 37° C. Thereafter, the medium containing the cells was transferred to a 5 ml tube, centrifuged to remove the supernatant, and washed with PBS solution was repeated 3 times. Thereafter, Jurkat cells were suspended in 650 μl of PBS, and the fluorescence of the LRRC24P mutant-EGFP fusion proteins introduced into the cells through a flow cytometer was measured to confirm the intracellular introduction efficiency (FIG. 10). Through this, it was confirmed that the LRRC24P mutants showed a change in the introduction efficiency through mutation, but the cell-penetrating ability was maintained (FIG. 10).

What is claimed is:

1. Transmembrane domain consisting of any one of the polypeptides of SEQ ID NOs: 1 to 7, 21 and 22 derived from Human LRRC24 (Leucine rich repeat containing 24) protein.

2. A recombinant cargo having improved cell membrane permeability, comprising a cargo fused to the N-terminal or C-terminal of the transmembrane domain of claim 1.

3. The recombinant cargo of claim 2, wherein the cargo is a protein, nucleic acid, lipid or compound.

4. The recombinant cargo of claim 2, wherein the cargo is any one selected from the group of hormones, Immunoglobulin, antibody, structural protein, signaling peptide, storage peptide, membrane peptide, transmembrane peptide, internal peptide, external peptide, secretory peptide, viral peptide, native peptide, glycosylated protein, fragmented protein, Disulfide peptide, recombinant proteins, chemically modified proteins and prions.

5. The recombinant cargo of claim 2, wherein the cargo is any one selected from the group consisting of nucleic acids, coding nucleic acid sequences, mRNA, antisense RNA molecules, carbohydrates, lipids and glycolipids.

6. The recombinant cargo of claim 2, wherein the cargo is a contrast material, drug or chemical.

7. A gene construct comprising a polynucleotide encoding the transmembrane domain of claim 1.

8. An expression vector for expression of a recombinant cargo protein having improved cell membrane permeability comprising the gene construct of claim 7.

9. A method of delivering a cargo into a cell comprising the step of preparing a recombinant cargo in which cargo is fused to the N-terminus or C-terminus of the transmembrane domain of claim 1; and the step of contacting the prepared recombinant cargo with the isolated cells.

10. A method of delivering cargo into an animal comprising the step of preparing a recombinant cargo in which cargo is fused to the N-terminus or C-terminus of the transmembrane domain of claim 1; and the step of administering the prepared recombinant cargo to animals other than humans.

* * * * *

SEQUENCE LISTING

```
<160> NUMBER OF SEQ ID NOS: 37

<210> SEQ ID NO 1
<211> LENGTH: 10
<212> TYPE: PRT
<213> ORGANISM: Artificial Sequence
<220> FEATURE:
<223> OTHER INFORMATION: LRRC24P

<400> SEQUENCE: 1

Arg Arg Arg Arg Arg Arg Lys Lys Ala Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: LRRC24P-M1

<400> SEQUENCE: 2

Arg Arg Arg Arg Arg Arg Lys Lys Ser Arg
```

```
1               5                   10
```

<210> SEQ ID NO 3
<211> LENGTH: 10
<212> TYPE: PRT
<213> ORGANISM: Artificial Sequence
<220> FEATURE:
<223> OTHER INFORMATION: LRRC24P-M2

<400> SEQUENCE: 3

```
Arg Arg Arg Arg Arg Arg Lys Lys Val Arg
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: LRRC24P-M3

<400> SEQUENCE: 4

```
Arg Arg Arg Arg Arg Arg Lys Lys Tyr Arg
1               5                   10
```

<210> SEQ ID NO 5
<211> LENGTH: 10
<212> TYPE: PRT
<213> ORGANISM: Artificial Sequence
<220> FEATURE:
<223> OTHER INFORMATION: LRRC24P-M4

<400> SEQUENCE: 5

```
Arg Arg Arg Arg Arg Arg Lys Lys Glu Arg
1               5                   10
```

<210> SEQ ID NO 6
<211> LENGTH: 10
<212> TYPE: PRT
<213> ORGANISM: Artificial Sequence
<220> FEATURE:
<223> OTHER INFORMATION: LRRC24P-M5

<400> SEQUENCE: 6

```
Arg Arg Arg Arg Arg Arg Lys Lys Gln Arg
1               5                   10
```

<210> SEQ ID NO 7
<211> LENGTH: 10
<212> TYPE: PRT
<213> ORGANISM: Artificial Sequence
<220> FEATURE:
<223> OTHER INFORMATION: LRRC24P-M6

<400> SEQUENCE: 7

```
Arg Arg Arg Arg Arg Arg Lys Lys Arg Arg
1               5                   10
```

<210> SEQ ID NO 8
<211> LENGTH: 10
<212> TYPE: PRT
<213> ORGANISM: Artificial Sequence
<220> FEATURE:
<223> OTHER INFORMATION: LRRC24P-MN

<400> SEQUENCE: 8

```
Arg Arg Arg Arg Arg Arg Lys Lys Asn Arg
1               5                   10
```

```
<210> SEQ ID NO 9
<211> LENGTH: 10
<212> TYPE: PRT
<213> ORGANISM: Artificial Sequence
<220> FEATURE:
<223> OTHER INFORMATION: LRRC24P-MD

<400> SEQUENCE: 9

Arg Arg Arg Arg Arg Arg Lys Lys Asp Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: LRRC24P-MC

<400> SEQUENCE: 10

Arg Arg Arg Arg Arg Arg Lys Lys Cys Arg
1               5                   10

<210> SEQ ID NO 11
<211> LENGTH: 10
<212> TYPE: PRT
<213> ORGANISM: Artificial Sequence
<220> FEATURE:
<223> OTHER INFORMATION: LRRC24P-MG

<400> SEQUENCE: 11

Arg Arg Arg Arg Arg Arg Lys Lys Gly Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: LRRC24P-MH

<400> SEQUENCE: 12

Arg Arg Arg Arg Arg Arg Lys Lys His Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: LRRC24P-MI

<400> SEQUENCE: 13

Arg Arg Arg Arg Arg Arg Lys Lys Ile Arg
1               5                   10

<210> SEQ ID NO 14
<211> LENGTH: 10
<212> TYPE: PRT
<213> ORGANISM: Artificial Sequence
<220> FEATURE:
<223> OTHER INFORMATION: LRRC24P-ML

<400> SEQUENCE: 14

Arg Arg Arg Arg Arg Arg Lys Lys Leu Arg
1               5                   10
```

<210> SEQ ID NO 15
<211> LENGTH: 10
<212> TYPE: PRT
<213> ORGANISM: Artificial Sequence
<220> FEATURE:
<223> OTHER INFORMATION: LRRC24P-MK

<400> SEQUENCE: 15

Arg Arg Arg Arg Arg Arg Lys Lys Lys Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: LRRC24P-MM

<400> SEQUENCE: 16

Arg Arg Arg Arg Arg Arg Lys Lys Met Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: LRRC24P-MF

<400> SEQUENCE: 17

Arg Arg Arg Arg Arg Arg Lys Lys Phe Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: LRRC24P-MP

<400> SEQUENCE: 18

Arg Arg Arg Arg Arg Arg Lys Lys Pro Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: LRRC24P-MT

<400> SEQUENCE: 19

Arg Arg Arg Arg Arg Arg Lys Lys Thr Arg
1               5                   10

<210> SEQ ID NO 20
<211> LENGTH: 10
<212> TYPE: PRT
<213> ORGANISM: Artificial Sequence
<220> FEATURE:
<223> OTHER INFORMATION: LRRC24P-MW

<400> SEQUENCE: 20

Arg Arg Arg Arg Arg Arg Lys Lys Trp Arg
1               5                   10

```
<210> SEQ ID NO 21
<211> LENGTH: 9
<212> TYPE: PRT
<213> ORGANISM: Artificial Sequence
<220> FEATURE:
<223> OTHER INFORMATION: LRRC24P-M7

<400> SEQUENCE: 21

Arg Arg Arg Arg Arg Lys Lys Ala Arg
1               5

<210> SEQ ID NO 22
<211> LENGTH: 9
<212> TYPE: PRT
<213> ORGANISM: Artificial Sequence
<220> FEATURE:
<223> OTHER INFORMATION: LRRC24P-M8

<400> SEQUENCE: 22

Arg Arg Arg Arg Arg Arg Lys Lys Ala
1               5

<210> SEQ ID NO 23
<211> LENGTH: 30
<212> TYPE: DNA
<213> ORGANISM: Artificial Sequence
<220> FEATURE:
<223> OTHER INFORMATION: LRRC24P expression nucleic acid

<400> SEQUENCE: 23
cgccggcgcc gcaggcgaaa aaaggcgcgg                                          30

<210> SEQ ID NO 24
<211> LENGTH: 30
<212> TYPE: DNA
<213> ORGANISM: Artificial Sequence
<220> FEATURE:
<223> OTHER INFORMATION: LRRC24P synthesis nucleic acid

<400> SEQUENCE: 24
cgccgccgta gaagacgtaa aaaggcaaga                                          30

<210> SEQ ID NO 25
<211> LENGTH: 720
<212> TYPE: DNA
<213> ORGANISM: Artificial Sequence
<220> FEATURE:
<223> OTHER INFORMATION: LRRC24P EGFP nucleic acid

<400> SEQUENCE: 25
atggtgagca agggcgagga gctgttcacc ggggtggtgc ccatcctggt cgagctggac         60
ggcgacgtaa acggccacaa gttcagcgtg tccggcgagg gcgagggcga tgccacctac        120
ggcaagctga ccctgaagtt catctgcacc accggcaagc tgcccgtgcc ctggcccacc        180
ctcgtgacca ccctgaccta cggcgtgcag tgcttcagcc gctaccccga ccacatgaag        240
cagcacgact tcttcaagtc cgccatgccc gaaggctacg tccaggagcg caccatcttc        300
ttcaaggacg acggcaacta caagacccgc gccgaggtga agttcgaggg cgacaccctg        360
gtgaaccgca tcgagctgaa gggcatcgac ttcaaggagg acggcaacat cctggggcac        420
aagctggagt acaactacaa cagccacaac gtctatatca tggccgacaa gcagaagaac        480
ggcatcaagg tgaacttcaa gatccgccac aacatcgagg acggcagcgt gcagctcgcc        540
gaccactacc agcagaacac ccccatcggc gacggccccg tgctgctgcc cgacaaccac        600
```

```
tacctgagca cccagtccgc cctgagcaaa gaccccaacg agaagcgcga tcacatggtc    660
ctgctggagt tcgtgaccgc cgccgggatc actctcggca tggacgagct gtacaagtaa   720
```

<210> SEQ ID NO 26
<211> LENGTH: 15
<212> TYPE: DNA
<213> ORGANISM: Artificial Sequence
<220> FEATURE:
<223> OTHER INFORMATION: linker

<400> SEQUENCE: 26

```
ggaggtgggg gctcg                                                     15
```

<210> SEQ ID NO 27
<211> LENGTH: 13
<212> TYPE: PRT
<213> ORGANISM: Artificial Sequence
<220> FEATURE:
<223> OTHER INFORMATION: HIV TAT1

<400> SEQUENCE: 27

Gly Arg Lys Lys Arg Arg Gln Arg Arg Arg Pro Pro Gly
1               5                   10

<210> SEQ ID NO 28
<211> LENGTH: 9
<212> TYPE: PRT
<213> ORGANISM: Artificial Sequence
<220> FEATURE:
<223> OTHER INFORMATION: HIV TAT2

<400> SEQUENCE: 28

Arg Lys Lys Arg Arg Gln Arg Arg Arg
1               5

<210> SEQ ID NO 29
<211> LENGTH: 11
<212> TYPE: PRT
<213> ORGANISM: Artificial Sequence
<220> FEATURE:
<223> OTHER INFORMATION: HIV TAT3

<400> SEQUENCE: 29

Tyr Gly Arg Lys Lys Arg Arg Gln Arg Arg
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Penetratin

<400> SEQUENCE: 30

Arg Gln Ile Lys Ile Trp Phe Gln Asn Arg Arg Met Lys Trp Lys Lys
1               5                   10                  15

<210> SEQ ID NO 31
<211> LENGTH: 27
<212> TYPE: PRT
<213> ORGANISM: Artificial Sequence
<220> FEATURE:
<223> OTHER INFORMATION: HIV glycoprotein 41 derived MPG

<400> SEQUENCE: 31

Gly Ala Leu Phe Leu Gly Phe Leu Gly Ala Ala Gly Ser Thr Met Gly

```
                1               5                   10                  15
Ala Trp Ser Gln Pro Lys Lys Lys Arg Lys Val
            20                  25
```

<210> SEQ ID NO 32
<211> LENGTH: 28
<212> TYPE: PRT
<213> ORGANISM: Artificial Sequence
<220> FEATURE:
<223> OTHER INFORMATION: BPrPr

<400> SEQUENCE: 32

```
Met Val Lys Ser Lys Ile Gly Ser Trp Ile Leu Val Leu Phe Val Ala
1               5                   10                  15
Met Trp Ser Asp Val Gly Leu Cys Lys Lys Arg Pro
            20                  25
```

<210> SEQ ID NO 33
<211> LENGTH: 11
<212> TYPE: PRT
<213> ORGANISM: Artificial Sequence
<220> FEATURE:
<223> OTHER INFORMATION: Hph-1

<400> SEQUENCE: 33

```
Tyr Ala Arg Val Arg Arg Arg Gly Pro Arg Arg
1               5                   10
```

<210> SEQ ID NO 34
<211> LENGTH: 11
<212> TYPE: PRT
<213> ORGANISM: Artificial Sequence
<220> FEATURE:
<223> OTHER INFORMATION: NP2

<400> SEQUENCE: 34

```
Lys Ile Lys Lys Val Lys Lys Lys Gly Arg Lys
1               5                   10
```

<210> SEQ ID NO 35
<211> LENGTH: 11
<212> TYPE: PRT
<213> ORGANISM: Artificial Sequence
<220> FEATURE:
<223> OTHER INFORMATION: TAT(p.18)

<400> SEQUENCE: 35

```
Tyr Gly Arg Lys Lys Arg Arg Gln Arg Arg Arg
1               5                   10
```

<210> SEQ ID NO 36
<211> LENGTH: 11
<212> TYPE: PRT
<213> ORGANISM: Artificial Sequence
<220> FEATURE:
<223> OTHER INFORMATION: Hph-1(p.19)

<400> SEQUENCE: 36

```
Tyr Ala Arg Val Arg Arg Arg Gly Pro Arg Arg
1               5                   10
```

<210> SEQ ID NO 37
<211> LENGTH: 11
<212> TYPE: PRT
<213> ORGANISM: Artificial Sequence
<220> FEATURE:

<223> OTHER INFORMATION: NP2(p.19)

<400> SEQUENCE: 37

Lys Ile Lys Lys Val Lys Lys Lys Gly Arg Lys
1               5                   10